(12) United States Patent  (10) Patent No.: US 8,032,947 B1
Gait                      (45) Date of Patent:     Oct. 11, 2011

(54) FLEX FIT EYEWEAR (75) Inventor: Paul Gait, Altamont, NY (US)

(73) Assignee: Rawlings Sporting Goods Company, Inc., St. Louis, MO (US)

( * ) Notice: Subject to any disclaimer, the term of this patent is extended or adjusted under 35 U.S.C. 154(b) by 325 days.

(21) Appl. No.: 12/129,564

(22) Filed: May 29, 2008

Related U.S. Application Data

(60) Provisional application No. 60/940,608, filed on May 29, 2007.

(51) Int. Cl.
A61F 9/00 (2006.01)
A61F 9/02 (2006.01)
A42B 1/08 (2006.01)
A63B 71/10 (2006.01)
A41D 13/00 (2006.01)

(52) U.S. Cl. ............... 2/15; 2/424; 2/425; 2/426; 2/9

(58) Field of Classification Search .......... 2/424, 425, 2/15, 10, 11, 12, 13, 426, 427, 428, 429, 2/430, 431, 432, 433, 434, 435, 436, 437, 2/438, 439, 440, 441, 442, 443, 444, 445, 2/446, 447, 448, 449, 450, 451, 452, 9; D29/102, D29/104, 105, 106, 107
See application file for complete search history.

(56) References Cited

U.S. PATENT DOCUMENTS

| 2,422,534 | A  |   | 1/1944  | Du Bois |
| 2,526,181 | A  | * | 10/1950 | Wilen ............................ 2/440 |
| 2,556,847 | A  | * | 6/1951  | MacLean ........................ 2/436 |
| 2,612,640 | A  | * | 10/1952 | Palmes .......................... 2/436 |
| 2,636,171 | A  | * | 4/1953  | Aspenleiter .................... 2/436 |
| 2,881,444 | A  | * | 4/1959  | Fresh et al. ...................... 2/9 |
| 2,907,041 | A  | * | 10/1959 | Finn ............................. 2/432 |
| 3,530,506 | A  |   | 9/1970  | Hoffmaster |
| 4,021,878 | A  | * | 5/1977  | Peillex .................... 15/250.28 |
| 4,024,405 | A  | * | 5/1977  | Szot ........................ 250/516.1 |
| 4,173,795 | A  | * | 11/1979 | Lundin et al. ................... 2/425 |
| 4,784,131 | A  | * | 11/1988 | Schroeder ............... 128/206.16 |
| 6,149,268 | A  | * | 11/2000 | Hall et al. ....................... 351/62 |
| 6,227,664 | B1 | * | 5/2001  | Pavlak ........................... 351/62 |
| 6,460,196 | B2 | * | 10/2002 | Tsubooka et al. .............. 2/428 |
| 6,564,804 | B2 | * | 5/2003  | Salatka et al. ............... 128/857 |
| 7,127,747 | B2 |   | 10/2006 | Darnell et al. |
| 7,181,779 | B2 |   | 2/2007  | Hussey |
| 7,188,625 | B2 | * | 3/2007  | Durette ........................ 128/858 |
| 7,797,765 | B2 | * | 9/2010  | Musal et al. .................... 2/448 |
| 2003/0145368 | A1 | * | 8/2003 | Johnson .......................... 2/434 |
| 2004/0133958 | A1 |   | 7/2004 | Darnell et al. |
| 2004/0148684 | A1 | * | 8/2004 | Wiedner ......................... 2/428 |

(Continued)

FOREIGN PATENT DOCUMENTS

FR 2684292 A1 * 6/1993

(Continued)

*Primary Examiner* — Gary L Welch
*Assistant Examiner* — Jane Yoon
(74) *Attorney, Agent, or Firm* — Waddey & Patterson, P.C.; Phillip E. Walker (57) ABSTRACT

Protective flexible eyewear for, inter alia, providing for increased comfort and fit among a variety of users having different facial shapes.

25 Claims, 5 Drawing Sheets

U.S. PATENT DOCUMENTS

| | | | |
|---|---|---|---|
| 2006/0117449 A1* | 6/2006 | Hahn et al. | 2/9 |
| 2006/0132704 A1* | 6/2006 | Gait | 351/62 |
| 2006/0143766 A1* | 7/2006 | Ramsey | 2/15 |
| 2007/0130675 A1* | 6/2007 | Sheldon | 2/448 |
| 2007/0171358 A1* | 7/2007 | Gait | 351/62 |
| 2007/0277297 A1* | 12/2007 | Chiang | 2/426 |
| 2008/0216217 A1* | 9/2008 | Wang | 2/426 |
| 2008/0256688 A1* | 10/2008 | Bruce | 2/441 |

FOREIGN PATENT DOCUMENTS

| | | | |
|---|---|---|---|
| WO | WO 91/11159 | * | 8/1991 |
| WO | WO 94/16654 | * | 8/1994 |

* cited by examiner

FLEX FIT EYEWEAR

This Utility Patent Application claims benefit of previously filed provisional patent application No. 60/940,608 filed May 29, 2007 entitled Flex Fit Eyewear.

All patents and publications described or discussed herein are hereby incorporated by reference in their entirety.

BACKGROUND OF THE INVENTION

The present invention relates generally to protective eyewear especially protective eyewear for protecting a user's eyes during a sporting event. More particularly, the present invention relates to protective sports eyewear having a flexible base in combination with a rigid protective element to protect the eyes of a wearer from contact while maintaining a secure fit.

The current improvement to the protective eyewear enhances the protection of the wearer's eyes and versatility of the eyewear itself while also being more comfortable to wear for extended periods of time. Specifically, the current invention protects a wearer's eyes while allowing the frame to fit more closely to the wearer's head while still maintaining a rigid protective element which may optionally be removed or replaced as desired by the wearer.

It will be appreciated by those skilled in the art that protective eyewear for sporting events has existed for years. However, most protective eyewear includes frames and/or lens elements which do not flex to fit a wide variety of different users' facial shapes, and thus, are not comfortable for a wide variety of users. Furthermore, many of these types of protective eyewear used in other fields, including contact sports, may become uncomfortable for a variety of different wearers as the eyewear does not fit closely to the user's face, and furthermore, may actually hamper the wearer's performance as the eyewear may be a source of irritation or distraction. For example, in Du Bois, U.S. Pat. No. 2,422,534 there is disclosed a protective eye shield which includes a curved frame and a flat lens piece used to protect the wearer's eyes.

In U.S. Pat. No. 3,530,506 Hoffmaster, there is disclosed a safety goggle having a readily attachable and replaceable lens and includes a fixed sized base for contact with the user's face.

In Hussey (U.S. Pat. No. 7,181,779) a sports goggle is disclosed with venting so as to provide for ventilation for the user. Allegedly, the goggle incorporates a system of high and low pressure areas external to the goggle to increase ventilation of the enclosed eye cavity to prevent fogging of the goggle lens.

Darnell et al., U.S. Pat. No. 7,127,747, discloses a protective eye mask for sports including a horizontal frame member forming an eye mask frame which defines a cage and a frame having at least an upper frame and lower frame segments. Furthermore, the protective eye mask of the '747 patent provides an improved eyewear device for addressing problems inherent from resulting impacts while also precluding fogging or otherwise impeding a user's vision during game play of a sport such as lacrosse.

Unfortunately, the conventional prior art eyewear does not have the structure to adequately fit a variety of faces of individuals of a participant of a sporting event and needs to be more comfortable to wear while also providing protection to the user's eyes. This prior art eyewear is composed of materials that would not adequately flex, bend, or shape to fit comfortably around the face of users and protect the eyes of participants in a sport such as lacrosse, hockey, football, or the like. For example, the conventional eyewear of the prior art lacks a multi-piece frame design while incorporating rigid protective elements which are necessary to protect the eyes of a participant from impact with solid objects at high speeds of which may occur during participation in a sporting event.

Accordingly, there is a need for protective eyewear which adequately protects a wearer's eyes while being comfortable to wear by a variety of users with different facial shapes. Furthermore, there is a need for protective eyewear which provides for an unimpeded vision while being comfortable to wear for the extended amount of time necessary for participation in a sport or the like.

BRIEF SUMMARY OF THE INVENTION

The present invention provides a protective eyewear for protecting a wearer's eyes during a sporting event. The protective eyewear comprises a flexible frame and a rigid protective section. The frame includes at least a top support, a pair of armatures, connections for a rigid protective element, and comprises a multi-piece design allowing for greater flex of the frame. The rigid protection section includes at least a perimeter and a flat extension attached to the perimeter and shape which may optionally be removably engaged to the connection in the frame. Additionally, the metal protective section may embody a plurality of substantially aligned elongated bars horizontally segmenting the rigid protective section. Furthermore, the rigid protective section may include metals, hard composites, or the like and can also embody a plurality of cross members vertically positioned connecting across the rigid protective section which provides protection to the eyes of the wearer.

Preferably the protective eyewear comprises a multiple piece frame providing for the frame to have the flexibility to contour to a variety of different facial shapes of users. The frame may have crescent-shaped incisions about the left portion and right portion of the frame and a connection point for the strap so that the rigid protective element is maintained wherein the frame flexes around the face. In further embodiments, the frame may include a multi-piece design wherein the frame flexes about a joint in the frame thus providing closer contact with the user's face resulting in superior comfort. Additionally, the rigid protective section which may include a plurality of substantially aligned elongated bars is contained within the connection point of the frame with the frame flexing independently from the rigid protective section, to the user's face.

Preferably, the protective eyewear comprises a somewhat round, rigid protective section, preferably metal, in a grid-like pattern welded to a flat extension. The flat extension projects beyond the perimeter of the round, rigid protective section and can removably engage a groove within the flexible frame. Alternatively, the rigid protective section can be permanently attached to the flexible frame. Such combination of a flat extension for engaging the frame combined with the flexibility of the frame and round, rigid protective elements provide a much improved fit for the user of the eyewear while maintaining a high level of protection for the user's eyes and can also facilitate separation, replacement, and aesthetic change for the inventive eyewear.

In further embodiments, the flexible frame can also be designed so that the armatures form a generally convex shape and are shaped to substantially encompass the wearer's eyes rather than extend only around the sides of the wearer's eyes.

Advantageously, to produce the improved eyewear, a flexible frame is utilized including incisions, flexation points or the use of multi-components in comprising the frame with a rigid protective element so that a wearer experiences improved comfort while wearing the inventive eyewear.

An object of the invention therefore is protective eyewear having characteristics which enable it to be both protective and comfortable during the engagement of a sporting activity or the like.

Another object of the invention is a protective eyewear having a rigid protective section for providing protection from impact to the user's eyes.

Still another object of the invention is a protective eyewear having a multi-component frame so as to better conform to the facial shape of a user.

Yet another object of the invention is a protective eyewear having a flexible design incorporating specifically placed incisions so that the frame contours more closely to the facial shape of the user and provides greater comfort and securement.

These aspects and others that will become apparent to the artisan upon review of the following description can be accomplished by providing a protective eyewear having a flexible frame which conforms to the various facial shapes of different wearers and that can either permanently or removably engage a rigid protective section for protecting the user's eyes from impacts or blows.

DETAILED DESCRIPTION OF THE PREFERRED EMBODIMENTS

Figure 1:
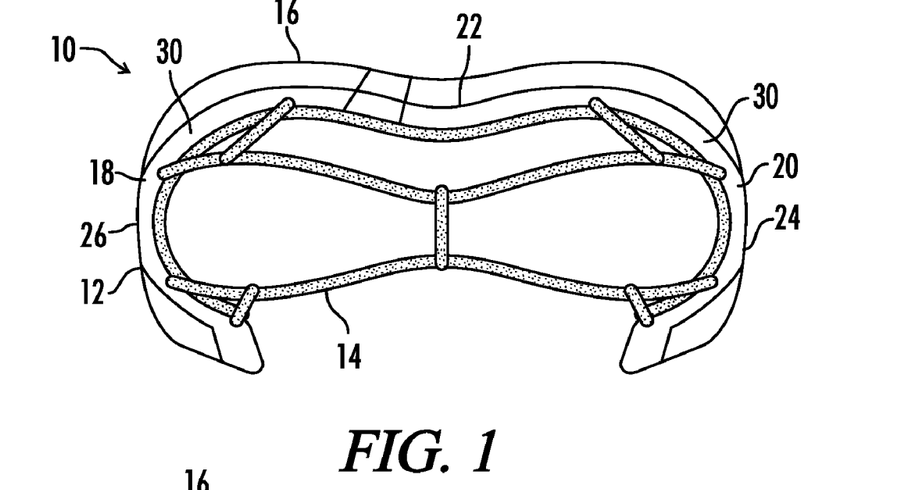
FIG. 1 is a front view of a first embodiment of the protective eyewear.

Referring generally now to FIG. 1, the first embodiment of the protective eyewear is shown and generally designated by the number 10. Protective eyewear 10 is for protecting the eyes of a participant in a sporting event or other similar activities where protection for the eyes is necessary. The participant which can also be described as a wearer, positions protective eyewear 10 on his or her head such that the eyes are protected. Generally, protective eyewear 10 comprises frame 12 and rigid protective section 14.

Frame 12 includes top support 16, pair of armatures 18 and 20, and connection point 22. Connection point 22 can also be described as a grooved opening, an opening, a slot or any other connection point which traverses top support 16 and may traverses each armature 18 and 20. Top support 16 at armatures 18 and 20 form a generally convex shape although are not limited to a convex shape and are furthermore typically shaped to substantially encompass the eyes of the wearer.

Figure 2:
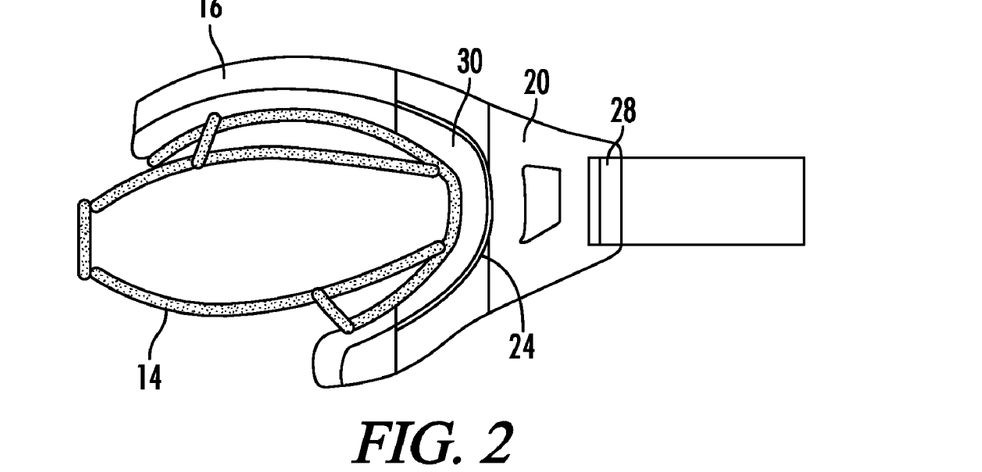
FIG. 2 is a side view of a first embodiment of the protective eyewear.

Armatures 18 and 20 further include flexation points 24 and 26 as well as attachment point 28. Generally, the armatures are defined as the portion of the frame on each side of the rigid protective section, separated by the top support. As more easily illustrated in FIG. 2, flexation point 24 as well as flexation point 26 (not shown) comprise in this embodiment a slit which provides for flexibility in armature 18 and armature 20 of protective eyewear 10. Generally flexation point 24 may embody a slit, a less dense area of the armatures, a perforation, a stretchable material, among other embodiments which provide for flexing of the frame at the flexation point.

Generally, rigid protection element 14 is substantially non-flexible as it is necessary to be rigid to provide the protection against impacts and blows during participation in this sport or the like. As such, when connected to frame 12 at connection point 22, rigid protection element 14 precludes the portion of frame 12 connected to rigid protection element 14 from flexing. By including flexation points 24 and 26, adjacent frame element 30 maintains an adjacent position to rigid protection element 14 whereas the portion of frame 12 opposite flexation points 24 and 26 may flex and bend nearer to the user's face.

Frame 12 is typically comprised of a flexible material such as a soft polyurethane that can be used to cushion the engagement of the frame to the head of the wearer while also flexing at flexation point 24 and 26 to maintain a secure and comfortable contact to the wearer. Additionally, the use of a soft polyurethane material or other soft polymer allows for a slight expansion to engage rigid protective element 14 to frame 12 of protective eyewear 10 for use, and furthermore, also allows for the removal and assembly of the protective eyewear.

Figure 3:
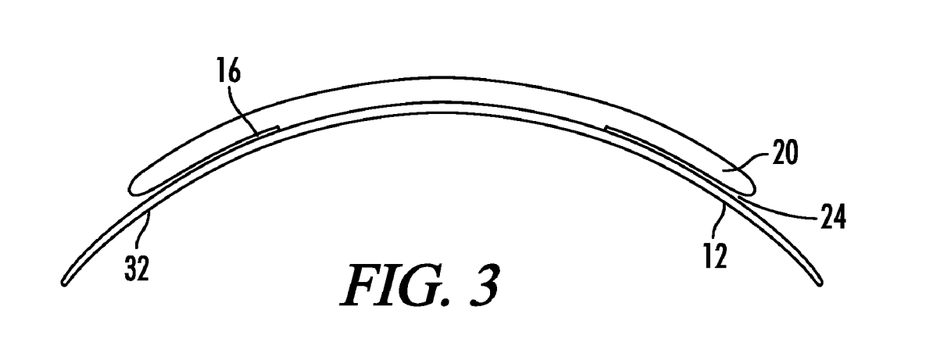
FIG. 3 is a top view of a first embodiment of the protective eyewear.

As further illustrated in FIG. 3 is an embodiment of frame 12 of protective eyewear 10 without attached rigid protective element 14 to protective eyewear 10. In this embodiment, frame 12 may be more specifically described as including adjacent frame segment 30 which may engage rigid protective element 14 and also facial contact portion 32 for contact with the wearer's face. Between facial contact element 32 and adjacent frame element 30 of frame 12 is flexation points 24 and 26 wherein facial contact portion 32 can flex away from adjacent frame element 30 so as to better conform to the wearer's face. In further embodiments not illustrated, facial contact portion 32 and adjacent frame element 30 are one continuous piece with flexation points 24 and 26 cut into frame 12 to construct adjacent frame element 30 and facial contact portion 32. However, in FIG. 3 as illustrated, frame 12 can include adjacent frame element 30 which may be adhered or otherwise attached in a variety of manners including adhesives, heat fixation, plugs or other physical attachments to facial contact portion 32 to comprise frame 12 having a flexible feature.

Figure 4:
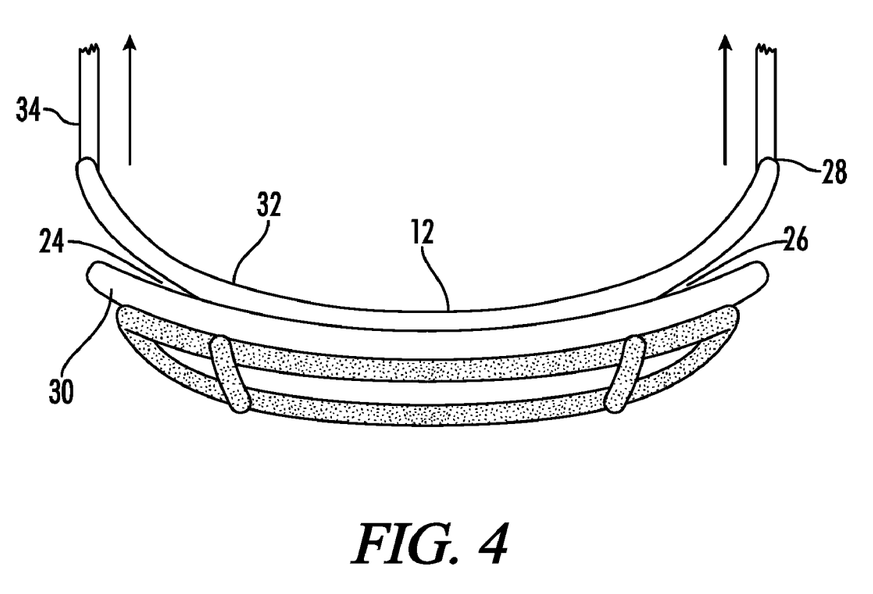
FIG. 4 is a top view under tension of a first embodiment of the protective eyewear.

Now referring generally to FIG. 4, there is as illustrated, a first embodiment of protective eyewear 10 under a state of tension from strap 34 as would be realized upon a face of a wearer. Facial contact portions 32 flex away from adjacent frame element 30 and contour closely to the face of the wearer (not shown) resulting from the tension applied to strap 34 connected to frame 12 at attachment points 28 wherein the wearer's eyes would still be substantially protected by rigid protection element 14 connected at connection point 22 to adjacent frame element 30. More specifically, flexation point 24 and flexation point 26 embodied as either a gap, slit, opening, flexible material or any other style which provides for the flexation of the frame with the facial contact portion 32, are flexible from the adjacent frame portion of protective eyewear 10. Dependent upon the facial shape of the wearer, facial contact portion 32 may flex an even greater distance so as to remain in secure contact with the face of the individual wearer. For instance, a wearer with a smaller face will result in facial contact portion 32 flexing farther away at flexation points 24 and 26 from adjacent frame element 30 where conversely, a user with a larger facial shape will result in facial contact portions 32 being closer to adjacent frame portion 30 as flexation points 24 and 26 will not be required to flex near as much.

Figure 5:
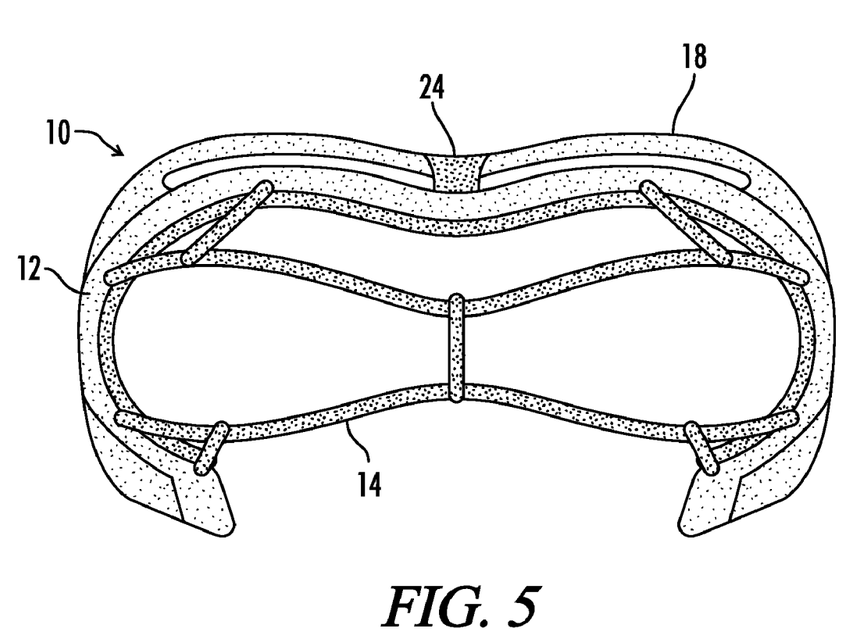
FIG. 5 is a front view of a second embodiment of the protective eyewear.
Figure 6:
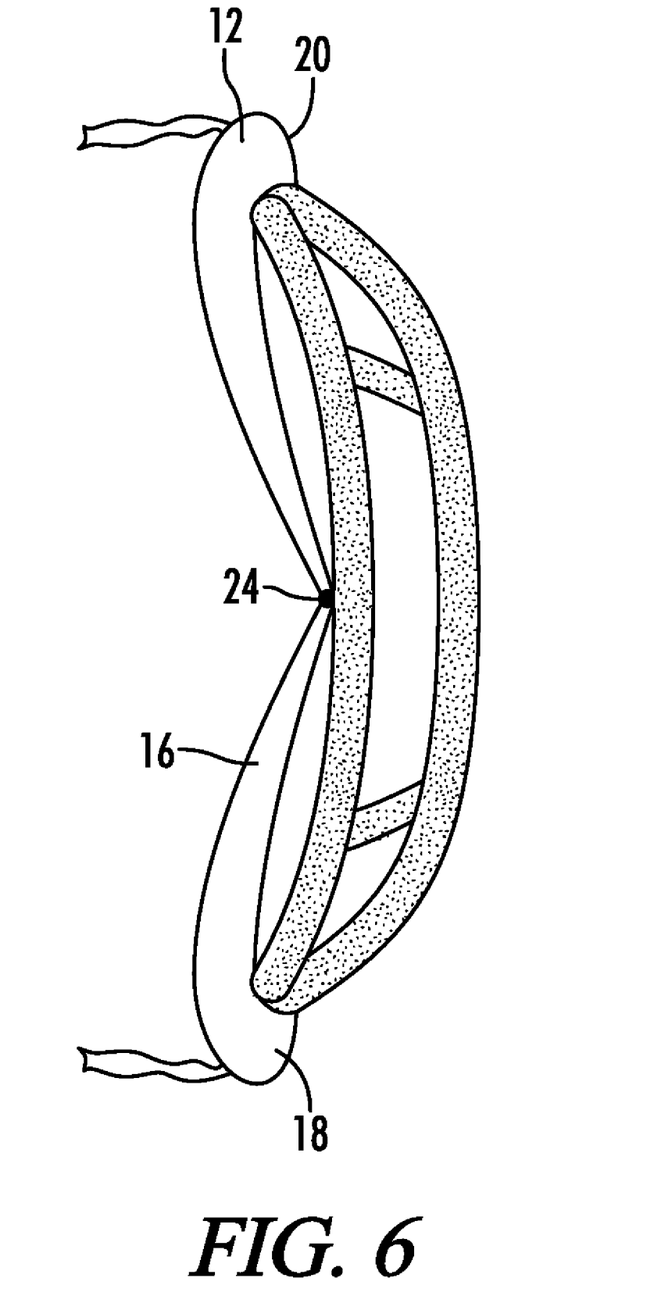
FIG. 6 is a top view of a second embodiment of the protective eyewear.

Referring now to FIG. 5, there is illustrated a further embodiment of protective eyewear 10 with a single flexation point in frame 12. More specifically, flexation point 24 is located in an approximate middle of frame 12 and provides a slight flexation about the wearer's forehead when the wearer has the protective eyewear positioned on their face. As such, the soft frame 12 flexes more so at flexation point 24 allowing for a more secure fit about the user's face. Furthermore, as seen in a top view of FIG. 6, rigid protection element 14 is secured primarily to frame 12 at armature 18 and at armature 20 with an open space partially between top support 16 of frame 12 and rigid protection element 14. This allows for flexation point 24 to flex thus allowing frame 12 to contour about the user's head thus providing a comfortable fit while still maintaining rigid protective element 14 about the eyes of the wearer.

Figure 7:
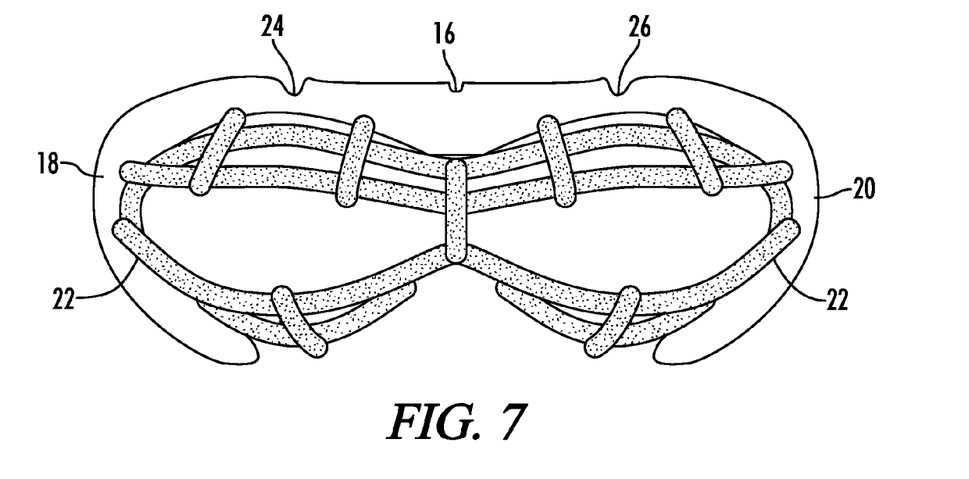
FIG. 7 is a front view of a third embodiment of the protective eyewear.

FIG. 7 illustrates a further embodiment of the novel protective eyewear including flexation points 24 and 26 on top support 16 of frame 12 of protective eyewear 10. In this embodiment, both flexation points 24 and 26 provide the capability of contouring closely to the user's forehead, and thus, may be adapted readily to users having different contours of their forehead. More specifically, flexation point 24 and flexation point 26 of an embodiment in FIG. 7 may be an indentation in the soft polyurethane or other polymeric material of frame 12 of protective eyewear 10 or may include a joint or may incorporate other materials dissimilar from the polyurethane used in the frame. A fabric connection or softer polymer as well as a hinged joint may be utilized at either flexation point 24 or 26 of FIG. 7 so as to provide flex in the frame while still maintaining rigid protective element 14 about the wearer's eyes. Additionally, in this embodiment, armatures 18 and 20 connect at connection point 22 to rigid protective element 14 wherein an opening may be provided between top support element 16 and rigid protective element 14 of protective eyewear 10. This at least partially open space may provide for greater flex of top support element 16 while still maintaining rigid protective element 14 securely connected at connection point 22 to armatures 18 and 20 of protective eyewear 10.

In all the above embodiments of the novel protective eyewear, the armatures may include features so that the rigid section is removable from the frame of the glasses. Typically securing depressions are used which rely on a pressure fit to properly fit the rigid section into the protective eyewear. In further embodiments, the rigid protection section may be affixed permanently to the frame and is not easily removable although in preferable embodiments, the rigid protective element is removable for repair, alterations, or esthetic enhancements.

In further embodiments a padded element may be on the portion of the frame closest to the user's face. This may be added to provide further comfort and may also aid in wicking sweat from the user. Such padded elements may include clothes including natural and artificial fibers, as well as foam materials and the like.

Additionally, this removably securable feature of the rigid protection section allows a wearer to replace individual components of the protective eyewear. Namely, the wearer can replace the frame independently from the rigid protective section and/or the rigid protection section independently of the frame. A wearer also has the ability to color coordinate the individual aspects of the protective eyewear as desired to match the frame and metal protection section to the team colors to which he or she is playing. Generally, the frame may be securely removable and attachable to the rigid protective section without the use of tools. This removable attachment is easily accomplished. A wearer can grasp a portion of the frame and pull that portion of the frame until the connection of the frame to the rigid protective element is uncoupled.

A variety of different arrangements of the rigid protective element can be utilized in the novel protective eyewear. For instance, different compositions including hard thermoplastics, polymers, rubbers, composites, metals, or metal alloys in combination thereof may be utilized in comprising the rigid protective element of the protective eyewear. Typically, the protective element is utilized to dissipate and preclude damage to the wearer's eyes from an impact or blow received during a sporting event or the like. As such, the rigid protective section must not shatter or deform easily under stress so as to render damage to the user's eyes.

Yet furthermore, the rigid protective section may include a variety of different embodiments and designs not included in FIGS. 1-7 and may include a variety of wire and/or metal designs known in the art. As such, the inventive protective eyewear may include rigid protective elements designed and described in U.S. patent application Ser. No. 11/694,952 entitled "Protective Eyewear with Metal Lenses" which is hereby incorporated by reference in its entirety.

The flexible protective eyewear of the present invention allows a multiplicity of players to use the same model of goggles irrespective of their different facial shapes as the protective eyewear can readily and easily conform to the facial shape of each wearer. As such, the present invention can be utilized comfortably for extended periods of time for a wide variety of people for sporting events such as lacrosse, hockey, or the like. The incorporation of flexation points provides for the use of a rigid protective element of one size to be used for a variety of differently sized users as the flexation points provide for a comfortable and secure fit for various sized individuals.

Accordingly, by the practice of the present invention, a flexible protective eyewear having heretofore unrecognized characteristics is created. The protective eyewear provides for greater flexibility and comfort during performance in a sporting event such as lacrosse, hockey, or the like wherein the protective eyewear has an improved fit to the user's individual face.

The disclosure of all cited patents and publications referred to in this application are incorporated by reference.

The above description is intended to enable the person skilled in the art to practice the invention. It is not intended to detail all the possible variations and modifications that will become apparent to the skilled worker upon reading the description. It is intended, however, that all such modifications and variations be included within the scope of the invention that is defined by the following claims. The claims are intended to cover the intended elements and steps that any arrangement or sequence that is effective to meet the objectives intended for the invention unless content specifically indicates the contrary.

What is claimed is:

1. Protective eyewear comprising:
    an eyewear frame with a pair of armatures, a top support, a connection point, a first end, and a second end;
    a securement strap connected to both the first end and the second end of the eyewear frame;
    a rigid protection section attached to the connection point of the eyewear frame with a first rigid end opposite to a second rigid end, the first rigid end nearer to the first end of the eyewear frame and the second rigid end nearer to the second end of the eyewear frame; and two flexation points in the eyewear frame for providing a comfortable fit to a user, a first flexation point between the eyewear frame and the rigid protection section with the first end of the eyewear frame and the first rigid end extending beyond the first flexation point and a second flexation point between the eyewear frame and the rigid protection section with the second end of the eyewear frame and second rigid end extending beyond the second flexation point, with flexation points on each armature.

2. The eyewear of claim 1 further comprising at least one flexation point on the top support of the eyewear frame.

3. The eyewear of claim 2 wherein the top support of the eyewear frame includes two flexation points.

4. The eyewear of claim 1 wherein the frame comprises a polymer.

5. The eyewear of claim 4 wherein the frame comprises polyurethane.

6. The eyewear of claim 1 wherein at least one flexation point comprises a slit.

7. The eyewear of claim 1 wherein at least one flexation point comprises a stretchable material.

8. The eyewear of claim 1 wherein at least one flexation point comprises an opening.

9. The eyewear of claim 1 wherein the rigid protective section comprises a wire structure.

10. The eyewear of claim 1 further comprising the rigid protective section permanently attached to the connection point of the eyewear frame.

11. The eyewear of claim 1 further comprising the rigid protective section removably attached to the connection point of the eyewear frame.

12. The eyewear of claim 1 wherein the frame further comprises attachment points for a securing strap.

13. The eyewear of claim 1 further comprising a padded element on the eyewear frame for contact with the user.

14. Protective eyewear comprising:
an eyewear frame with a pair of armatures, a top support, a connection point, a first end, and a second end;
a securement strap connected to both the first end and the second end of the eyewear frame;
a rigid protection section attached to the connection point of the eyewear frame with a first rigid end opposite to a second rigid end, the first rigid end nearer to the first end of the eyewear frame and the second rigid end nearer to the second end of the eyewear frame, the rigid protective section permanently attached to the connection point of the eyewear frame; and
two flexation points in the eyewear frame for providing a comfortable fit to a user, a first flexation point between the eyewear frame and the rigid protection section with the first end of the eyewear frame and the first rigid end extending beyond the first flexation point and a second flexation point between the eyewear frame and the rigid protection section with the second end of the eyewear frame and second rigid end extending beyond the second flexation point.

15. The eyewear of claim 14 further comprising at least one flexation point on the top support of the eyewear frame.

16. The eyewear of claim 15 wherein the top support of the eyewear frame includes two flexation points.

17. The eyewear of claim 14 wherein the frame comprises a polymer.

18. The eyewear of claim 17 wherein the frame comprises polyurethane.

19. The eyewear of claim 14 further comprising flexation points on each armature.

20. The eyewear of claim 14 wherein at least one flexation point comprises a slit.

21. The eyewear of claim 14 wherein at least one flexation point comprises a stretchable material.

22. The eyewear of claim 14 wherein at least one flexation point comprises an opening.

23. The eyewear of claim 14 wherein the rigid protective section comprises a wire structure.

24. The eyewear of claim 14 wherein the frame further comprises attachment points for a securing strap.

25. The eyewear of claim 14 further comprising a padded element on the eyewear frame for contact with the user.

\* \* \* \* \*